(12) United States Patent
Eggert et al.

(10) Patent No.: US 9,504,793 B2
(45) Date of Patent: Nov. 29, 2016

(54) MEDICAMENT DELIVERY DEVICE WITH CARTRIDGE SENSOR AND CARTRIDGE HOLDER DOOR SENSOR AND METHOD OF CONTROLLING THE DEVICE

(75) Inventors: Ilona Eggert, Frankfurt am Main (DE); Christopher Nigel Langley, Warwickshitre (GB); Shane Alistair Day, Warwickshire (GB); Aled Meredydd James, West Midlands (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 458 days.

(21) Appl. No.: 14/119,210

(22) PCT Filed: May 24, 2012

(86) PCT No.: PCT/EP2012/059751
§ 371 (c)(1),
(2), (4) Date: Nov. 21, 2013

(87) PCT Pub. No.: WO2012/160159
PCT Pub. Date: Nov. 29, 2012

(65) Prior Publication Data
US 2014/0188075 A1 Jul. 3, 2014

(30) Foreign Application Priority Data

May 25, 2011 (EP) .................................... 11167533

(51) Int. Cl.
*A61M 5/00* (2006.01)
*A61M 5/50* (2006.01)
(Continued)

(52) U.S. Cl.
CPC ............ *A61M 5/5086* (2013.01); *A61M 5/20* (2013.01); *A61M 5/24* (2013.01); *A61M 5/31543* (2013.01);
(Continued)

(58) Field of Classification Search
CPC .................. A61M 2205/50; A61M 2205/14; A61M 5/19; A61M 5/5086; A61M 2005/31588; A61M 2205/276; A61M 2205/6027; A61M 2205/502; A61M 2205/60; A61M 5/31535; A61M 5/31543; A61M 5/50
See application file for complete search history.

(56) References Cited

U.S. PATENT DOCUMENTS

| | | | |
|---|---|---|---|
| 2003/0161744 A1 | 8/2003 | Vilks et al. | |
| 2007/0197968 A1* | 8/2007 | Pongpairochana et al. | A61M 5/20 604/131 |

FOREIGN PATENT DOCUMENTS

| | | |
|---|---|---|
| JP | H10-511014 | 10/1998 |
| WO | 96/14097 | 5/1996 |
| WO | 98/01168 | 1/1998 |

(Continued)

OTHER PUBLICATIONS

International Search Report for Int. App. No. PCT/EP2012/059751, completed Aug. 22, 2012.
(Continued)

*Primary Examiner* — Emily Schmidt
(74) *Attorney, Agent, or Firm* — McDonnell Boehnen Hulbert & Berghoff LLP

(57) ABSTRACT

A medicament delivery device is presented for the administration of one or more drug agents, wherein the device comprises a retainer for holding a medicament cartridge. The retainer is moveable between an open and closed position. A position sensor for generating a position output is indicative of whether the retainer is in the open or closed position. Further, a cartridge sensor generates a cartridge output indicative of whether the retainer is holding a medicament cartridge. A controller controls a predetermined operation of the device in dependence on the output of the position sensor and on the output of the cartridge sensor.

8 Claims, 7 Drawing Sheets

(51) Int. Cl.
*A61M 5/315* (2006.01)
*A61M 5/20* (2006.01)
*A61M 5/24* (2006.01)
*A61M 5/34* (2006.01)
*A61M 5/142* (2006.01)

(52) U.S. Cl.
CPC .......... *A61M 5/2066* (2013.01); *A61M 5/2448* (2013.01); *A61M 5/34* (2013.01); *A61M 2005/14268* (2013.01); *A61M 2205/14* (2013.01); *A61M 2205/50* (2013.01); *A61M 2205/6018* (2013.01)

(56) References Cited

FOREIGN PATENT DOCUMENTS

| WO | 03/099357 | 12/2003 |
| WO | 2005/077441 | 8/2005 |
| WO | 2010/089310 | 8/2010 |

OTHER PUBLICATIONS

Chinese Office Action for CN App. No. 201280037491.6, issued Feb. 19, 2016.

* cited by examiner

MEDICAMENT DELIVERY DEVICE WITH CARTRIDGE SENSOR AND CARTRIDGE HOLDER DOOR SENSOR AND METHOD OF CONTROLLING THE DEVICE

CROSS REFERENCE TO RELATED APPLICATIONS

The present application is a U.S. National Phase application pursuant to 35 U.S.C. §371 of International Application No. PCT/EP2012/059751 filed May 24, 2012, which claims priority to European Patent Application No. 11167533.6 filed May 25, 2011. The entire disclosure contents of these applications are herewith incorporated by reference into the present application.

TECHNICAL FIELD

This invention relates to a medicament delivery device, and method of controlling the device, for the administration of one or more drug agents to a patient, and in particular but not exclusively, for the self-administration of the drug agent(s).

BACKGROUND

Certain disease states require treatment using one or more different medicaments. Some drug compounds need to be delivered in a specific relationship with each other in order to deliver the optimum therapeutic dose. Although the present patent application is applicable to single medicament devices, it is of benefit where combination therapy is desirable, but not possible in a single formulation for reasons such as, but not limited to, stability, compromised therapeutic performance and toxicology.

For example, in some cases it might be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of one or more medicament in a single injection or delivery step that is simple for the user to perform without complicated physical manipulations of the drug delivery device.

SUMMARY

In the case of a combination therapy device, the proposed drug delivery device provides separate storage containers or cartridge retainers for two or more active drug agents. These active drug agents are then only combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with the reservoir in the case of a single medicament device or, in the case of a combination therapy device, a primary reservoir and with a secondary reservoir of medicament containing at least one drug agent. The drug dispense interface can be a type of outlet that allows the two or more medicaments to exit the system and be delivered to the patient.

In practical use of medical devices of the above mentioned type, whether they be for single or plural medicament delivery, it is necessary to replace the drug containing reservoir, usually a cartridge, when the medicament(s) is/are exhausted.

A known medicament deliver device is provided with a retainer which is hinged to the device such as to be moved between an open and closed position. The retainer is configured to hold a medicament reservoir or cartridge. A latch is provided on the device for locking or holding the retainer in the closed position. Access to the retainer for loading or removing a medicament cartridge is achieved by releasing the latch. Prior to opening the retainer, it is important to ensure the absence of obstructions that may impede access to the retainer. For example, it is necessary to retract a piston rod from the medicament cartridge before moving the retainer to an open position to avoid damage to the device. A sensor may be provided for sensing whether the retainer door is in an open or closed position. However, the positioning of the sensor and/or logic programmed into the device control system in known devices can be such as to lead to transient states where there are inconsistencies between the actual and sensed state of the device. One example of this may be where the retainer is sensed as being open or closed but is in fact in transit between these states.

Positioning of the sensor in known devices may contribute to transient state conditions detracting from accurate sensing of the operating state of the device. For example, placement of the sensor on the door latch has led to transient state conditions. This arises because the retainer door activates the sensor on the latch as the door moves between the open and closed position.

The invention therefore faces the technical problem of ensuring an accurate determination of the state of the device and appropriate control logic to reduce risk of damage to the device arising from inconsistencies between the actual and sensed states of the device.

It is an aim of the present invention to alleviate the aforementioned difficulties. It is a further aim to simplify user operation of the medicament delivery device through the use of control logic. It is also an aim of the present invention to avoid unnecessary or inappropriate device functions taking place. It is a further aim of the present invention to devise a control logic that alleviates risk of error during operating sequences associated with replacement of medicament cartridges.

According to a first aspect of the present invention, there is provided a medicament delivery device for the administration of one or more drug agents, the device having a dispense interface for providing fluidic communication between an outlet and a medicament cartridge retainer, an interface sensor for generating an output indicative of whether the dispense interface is attached to or detached from the device, a controller for controlling a predetermined operation of the device in dependence on an output of the interface sensor.

In a preferred embodiment of the first aspect, the dispense interface is configured in this device for providing fluid communication from the device to an outlet. The outlet may include an attachment for a needle hub. The predetermined operation may relate to a cartridge change or replacement cycle of the device upon detachment of the interface sensor. In a preferred embodiment, the predetermined operation may be initiation of the cartridge change or replacement cycle.

According to a second aspect of the present invention, there is provided a medicament delivery device for the administration of one or more drug agents, wherein the device comprises a retainer for holding a medicament cartridge, the retainer being moveable between an open and closed position, a retainer sensor for sensing whether the retainer is in a closed or open position and for sensing presence or absence of a cartridge in the retainer, and a controller for controlling a predetermined operation of the device in dependence on an output of the retainer sensor.

The retainer sensor of a device embodying the present invention may comprise a position sensor for generating a position output indicative of whether the retainer is in an open or closed position, and a cartridge sensor for generating a cartridge output indicative of whether the retainer is holding a medicament cartridge. In a preferred embodiment, the controller facilitates control of different predetermined operation sequences depending on respective combinations of outputs from the retainer and position sensors. The predetermined operation may relate to identification (or not) of a medicament cartridge in the retainer.

The first and second aspects of the present invention may be utilised in a single or combination therapy device to make up a cartridge change or replacement cycle which may be programmed into software of the device controller. In a device embodying the first and second aspects, the first aspect is concerned with establishing user access to the medicament cartridge to be replaced, through opening of the retainer door, and the second aspect is concerned with device functionality following closure of the retainer door. The cartridge change or replacement cycle will be discussed further below.

As noted above, the first and second aspects are applicable to single therapy devices which have a single medicament stored in a single reservoir or cartridge. However, they are also applicable to combination therapy devices that can accommodate more than one drug agent reservoir or cartridge may include a first retainer and a second retainer for holding a medicament reservoirs or cartridges containing two drug agents that may be the same as or different from one another. The medicament reservoirs or cartridges may contain independent (single drug compound) or pre-mixed (co-formulated multiple drug compounds). The dispense interface for a device having first and second retainers may be provided with a bifurcated conduit for providing fluid communication from the first and second retainers to a unitary outlet. The needle hub may be removably attached to the unitary outlet. Each one of the first and second retainers may have an associated position sensor and cartridge sensor so that the cartridge change cycle of the device may be implemented in respect of each retainer separately.

The medicaments may be the same as or different from one another. The device may have a dose setting mechanism for user setting of an appropriate dose of the one or more drug agents. The retainer or each retainer in the case of a combination therapy device may have a drive train associated with it for automatic or manual delivery of the drug agent(s) to the patient. The drive train may include a piston rod for driving a bung of the medicament cartridge during a prime or dose operation of the device. The retainer and door may be coupled together or formed integrally as a unitary component of the device. The retainer is secured in a closed position by a latch which is movable between a latched and unlatched position under control of the controller. The retainer and/or door may be spring loaded so that on release of the latch by the controller, the retainer door opens such as to present the medicament cartridge held therein accessible to the user.

Devices embodying either aspect of the present invention may include a control panel with input means, such as buttons or the like, as well as output means, such as a digital display or a sound unit or the like. The input means may be configured to receive inputs from a user for dosing, priming functions and the like, whereas the output means may be configured to indicate information, permissible/disallowed functions, prompts or guidance to the user. The digital display may be configured to show if a cartridge retainer is open and which medicament reservoir, filled with what type of medicament, has to be inserted into the opened cartridge retainer. Likewise the digital display and the sound unit may be configured to indicate if a medicament reservoir has not properly been inserted into the respective cartridge retainer. The output means may further be configured to indicate information concerning the filling level of the medicament reservoirs.

The controller may include an electronic control unit that may comprise at least an evaluation unit, which is configured to receive signals from a sensor unit. In this configuration the sensor unit may be an electronic or an electromechanical sensor, which is configured to send signals to the evaluation unit dependant on the positions of the medicament or cartridge retainers and/or locking conditions of locking devices provided to retain the medicament reservoirs or cartridges in the device. There may also be a sensor unit, which is configured to send signals to the evaluation unit dependant on the correct insertion of the medicament reservoirs. There may further be a sensor unit, which is configured to send signals to the evaluation unit dependant on the filling level of the medicament reservoirs. The sensor units and the evaluation unit may also be one component.

When the dispense interface (i.e. cartridge hub) is detached or removed from the device, the controller responds to a signal generated by the interface sensor by initiating the cartridge change cycle. This comprises a step of activating a cartridge door button or buttons (i.e. one for each retainer) which may be provided on the device for opening the retainer door. When the cartridge door button is pressed by the user, the drive train rewinds to a 'home' end position and stops. This rewinding retracts the piston rod from the medicament cartridge held by the retainer. The piston rod is retracted to a position that is clear of the proximal end of the cartridge. The rewinding of the piston rod continues so that its travel goes beyond the proximal end to release the latch. This allows the retainer door to open under the action of the spring loading. A sensor is provided for detecting a retainer door open condition. The end position, i.e. fully retracted position, is reached by the piston rod and this is sensed by the controller. In response to this, the controller advances the drive train by a distance sufficient to move the latch into a position which permits locking of the retainer when the retainer door is closed after loading of the medicament cartridge. In a device embodying the first and second aspects, this sensor may be provided by the retainer sensor.

The operational procedure of devices embodying the second aspect of the present invention is invoked when the controller receives a signal from the position sensor, which in a preferred embodiment, may perform the function of a cartridge door switch. The operational procedure invoked depends on the output of the cartridge sensor that is received by the controller. In the event that the position sensor indicates that the retainer is closed and the cartridge sensor indicates that the retainer is holding a medicament cartridge, the drive train advances the piston rod towards the bung of the medicament cartridge until the drive train stalls. On stalling of the drive train, the controller may optionally implement a small rewind or 'back off' of the piston rod to reduce pressure on the medicament cartridge. A prompt is displayed on the display by the controller to advise the user of the operational status of the device. The prompt may include "Cartridge O.K." to signify a correct loading thereof, followed by a prompt to attach the dispense interface, such as "Fit Cartridge Hub". In a combination therapy device having two cartridge retainers, the prompt may provide the user with an option to select between changing the other cartridge (e.g. "Change Other Cartridge") or attaching the dispense interface. In the event that the user proceeds to attach the dispense interface, the controller may implement a mandatory priming operation to remove air from the dispense interface. In this case a prompt for the user to prime may be displayed.

In the event that the position sensor indicates that the retainer is closed and the cartridge sensor indicates that the retainer is not holding a medicament cartridge, a prompt (such as "Insert Cartridge") for the user to insert a medicament cartridge is displayed on the device. The display may present indicia to prompt the user to press the door open button for the relevant retainer, optionally providing an illustration or representation of a cartridge being inserted into the retainer. In a combination therapy device, the user may be given the option of removing the medicament cartridge from the other retainer as appropriate.

A need to replace a medicament cartridge, for example when the medicament is used up, may be indicated on the digital display. The controller software may check whether the interface hub is attached to the device. If it is, then the display presents a prompt for the user to remove the interface hub in order that the cartridge change cycle can be started.

According to a further aspect of the present invention, there is provided a method of controlling a medicament delivery device having a dispense interface, comprising: sensing detachment of the dispense interface from the device; sensing actuation of a cartridge door button in response to the sensed detachment of the dispense interface and retracting a piston rod from a medicament cartridge retainer of the device in response thereto; and opening the medicament cartridge retainer following retraction of the piston rod.

According to a still further aspect of the present invention, there is provided a method of controlling a medicament delivery device comprising: sensing outputs of a cartridge sensor and a medicament cartridge retainer position sensor; advancing the piston rod towards the medicament cartridge when the output of the cartridge sensor indicates the presence of a cartridge and the output of the medicament cartridge retainer position sensor indicates the retainer is in a closed position; or prompting insertion of a medicament cartridge when the output of the cartridge sensor does not indicate the presence of a cartridge when the position sensor indicates that the retainer is in the closed position.

According to a yet further aspect of the present invention, there is provided a method of controlling a medicament delivery device having a dispense interface, comprising: sensing detachment of the dispense interface from the device; sensing actuation of a cartridge door button in response to the sensed detachment of the dispense interface and retracting a piston rod from a medicament cartridge retainer of the device in response thereto; opening the medicament cartridge retainer following retraction of the piston rod; sensing outputs of a cartridge sensor and a medicament cartridge retainer position sensor; and either advancing the piston rod towards the medicament cartridge when the output of the cartridge sensor indicates the presence of a cartridge and the output of the medicament cartridge retainer position sensor indicates the retainer is in a closed position, or prompting insertion of a medicament cartridge when the output of the cartridge sensor does not indicate the presence of a cartridge when the position sensor indicates that the retainer is in the closed position.

According to a still further aspect of the present invention, there is provided a computer program, comprising code which when run on a processor, is operative to control a medicament delivery device for the administration of one or more drug agents, and to control the device to: sense outputs of a cartridge sensor and a medicament cartridge retainer position sensor; advance a piston rod towards the medicament cartridge when the output of the cartridge sensor indicates the presence of a cartridge and the output of the medicament cartridge retainer position sensor indicates the retainer is in a closed position; or prompt insertion of a medicament cartridge when the output of the cartridge sensor does not indicate the presence of a cartridge when the position sensor indicates that the retainer is in the closed position.

According to another aspect of the present invention, there is provided a computer-readable medium encoded with instructions that, when executed on a computer, control a medicament delivery device for the administration of one or more drug agents by: sensing outputs of a cartridge sensor and a medicament cartridge retainer position sensor; advancing the piston rod towards the medicament cartridge when the output of the cartridge sensor indicates the presence of a cartridge and the output of the medicament cartridge retainer position sensor indicates the retainer is in a closed position; or prompting insertion of a medicament cartridge when the output of the cartridge sensor does not indicate the presence of a cartridge when the position sensor indicates that the retainer is in the closed position.

In embodiments of either or both aspects of the present invention, the position sensor may be located in the device in a location that is separate from the retainer door latch.

Devices embodying one or both aspects of the present invention may guide the user through the sequence of operational steps of the device. This has the benefit of improving user operability by reducing risk of inappropriate, wrong or unbeneficial user selection of device functions. A further benefit lies in the avoidance of unnecessary motor movement with a consequential increase in battery life and avoiding wastage of dispense interfaces (cartridge hubs) or needle hubs.

The medicament delivery device may be an infusion device or an injection device, for example, a hand-held insulin injection pen. The medicament delivery devices embodying the present invention may be used either by medical personnel or by patients themselves. As an example, type-1 and type-2 diabetes may be treated by patients themselves by injection of insulin doses, for example once or several times per day. The first and second retainers may be configured to hold medicament reservoirs or cartridges that contain different drug agents from one another, for example, a fast acting insulin drug agent in one and a long acting insulin drug agent in the other. The first and second retainers are preferably sized differently from one another to ensure the user places the correct drug agent in the correct retainer. In embodiments of the present invention, the controller may be programmed by software to perform the operations of the device and to indentify the predetermined states and non-predetermined states of the device.

These as well as other advantages of various aspects of the present invention will become apparent to those of ordinary skill in the art by reading the following detailed description, with appropriate reference to the accompanying drawings.

DETAILED DESCRIPTION

Figure 1:
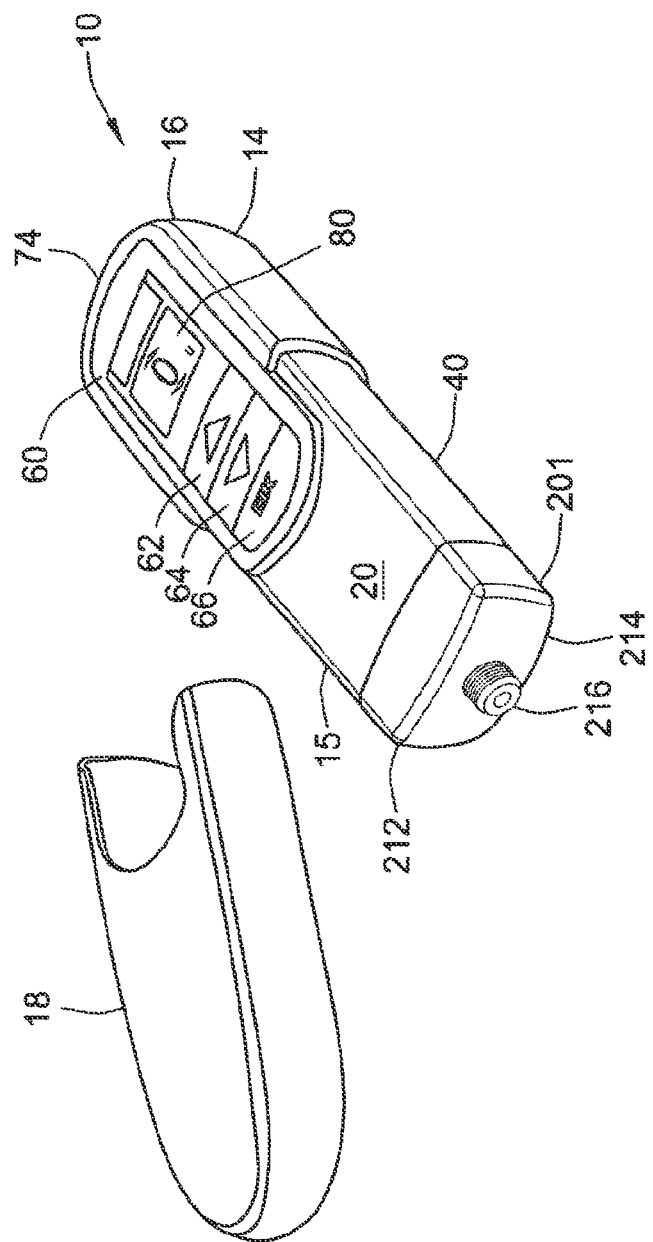
FIG. 1 illustrates a perspective view of a single medicament cartridge delivery device embodying the present invention with an end cap of the device removed.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and a single retainer for holding a medicament reservoir or cartridge. When the end cap or cover 18 is removed from the device 10 (as illustrated in FIG. 1), a dispense interface 201 is mounted to the distal end 15 of the main body 14, and a dose dispenser (e.g., a needle assembly) is attached to the interface. The dispense interface 201 provides a fluidic communication between the needle assembly and the medicament reservoir held within the device. The drug delivery device 10 can be used to administer a computed dose of a medicament through a single needle assembly.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK". In addition, along the most proximal end of the main body, an injection button 74 is also provided (not visible in the perspective view of FIG. 1). A cartridge holder 40 can be removably attached to the main body 14 and may contain a single cartridge retainer (not shown).

Figure 2:
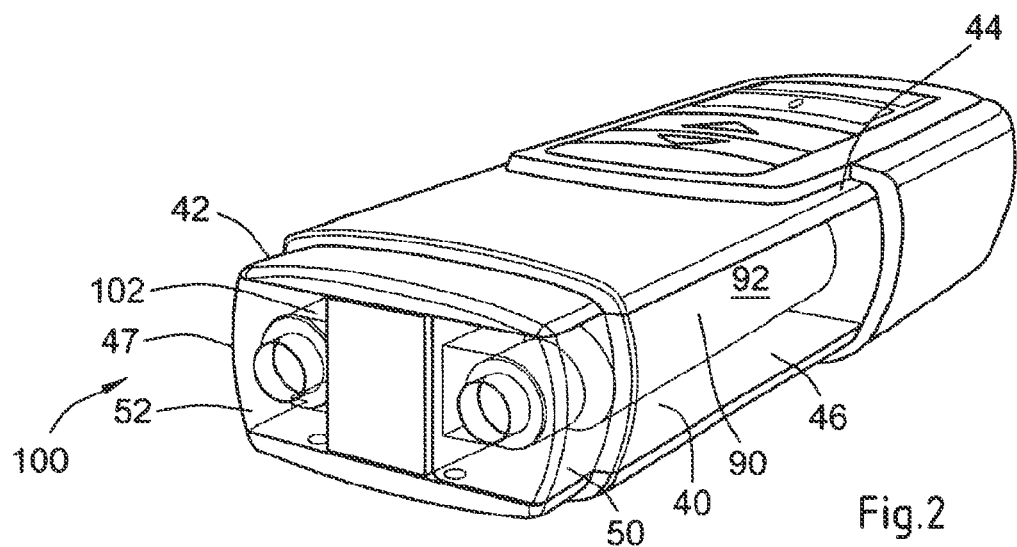
FIG. 2 illustrates a perspective view of the delivery device of FIG. 1 except that it has dual medicament cartridges.

The embodiment shown in FIG. 2, has similar elements to the embodiment of FIG. 1 except that the cartridge holder 40, which can also be removably attached to the main body 14, may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 2 includes a dispense interface 200 for providing fluidic communication between the needle assembly and the medicament reservoirs held within the device. In one arrangement, this dispense interface 200 includes a main outer body 212 that is removably attached to a distal end 42 of the cartridge holder 40. As for the embodiment of FIG. 1, a distal end 214 of the dispense interface 201 is similarly provided and preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 of the FIG. 1 and FIG. 2 embodiments illuminates and provides the user certain device information, preferably information relating to the medicament(s) contained within the cartridge holder 40. For example, the user is provided with certain information relating to the single medicament of FIG. 1 or both the primary medicament (Drug A) and the secondary medicament (Drug B) of FIG. 2.

Figure 3:
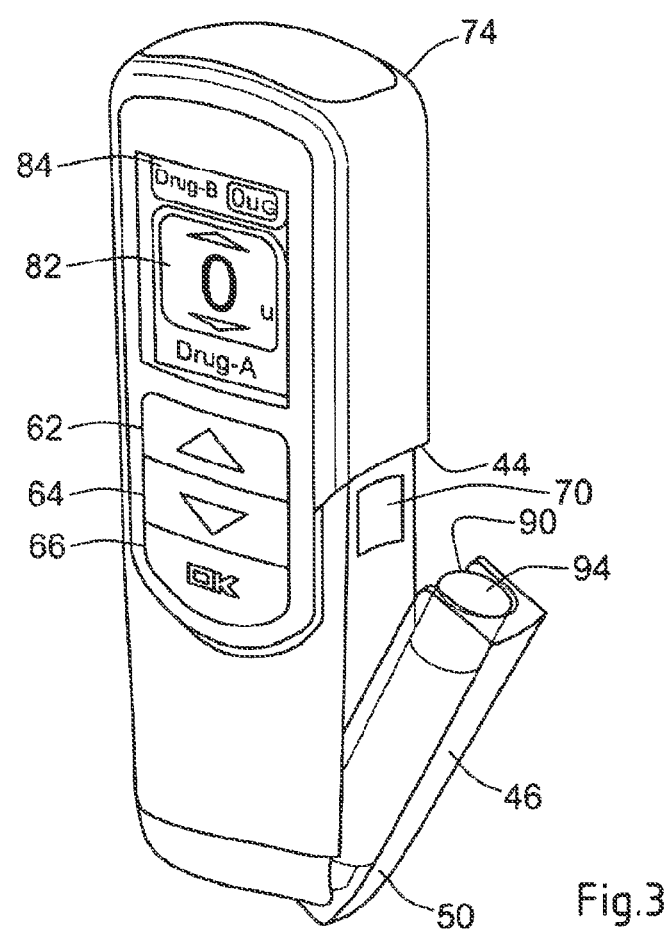
FIG. 3 illustrates a perspective view of the cartridge retainer illustrated in FIG. 2 with one cartridge retainer in an open position.

As shown in FIG. 3, first and second cartridge retainers 50, 52 comprise hinged cartridge retainers. These hinged retainers allow user access to the cartridges. FIG. 3 illustrates a perspective view of the cartridge holder 40 with the first hinged cartridge retainer 50 in an open position. FIG. 3 illustrates how a user might access the first cartridge 90 by opening up the first retainer 50 and thereby having access to the first cartridge 90. The cartridge holder 40 of FIG. 1 is provided with a single retainer similar to either retainer 50 or 52 of the embodiment of FIG. 2.

Figure 4:
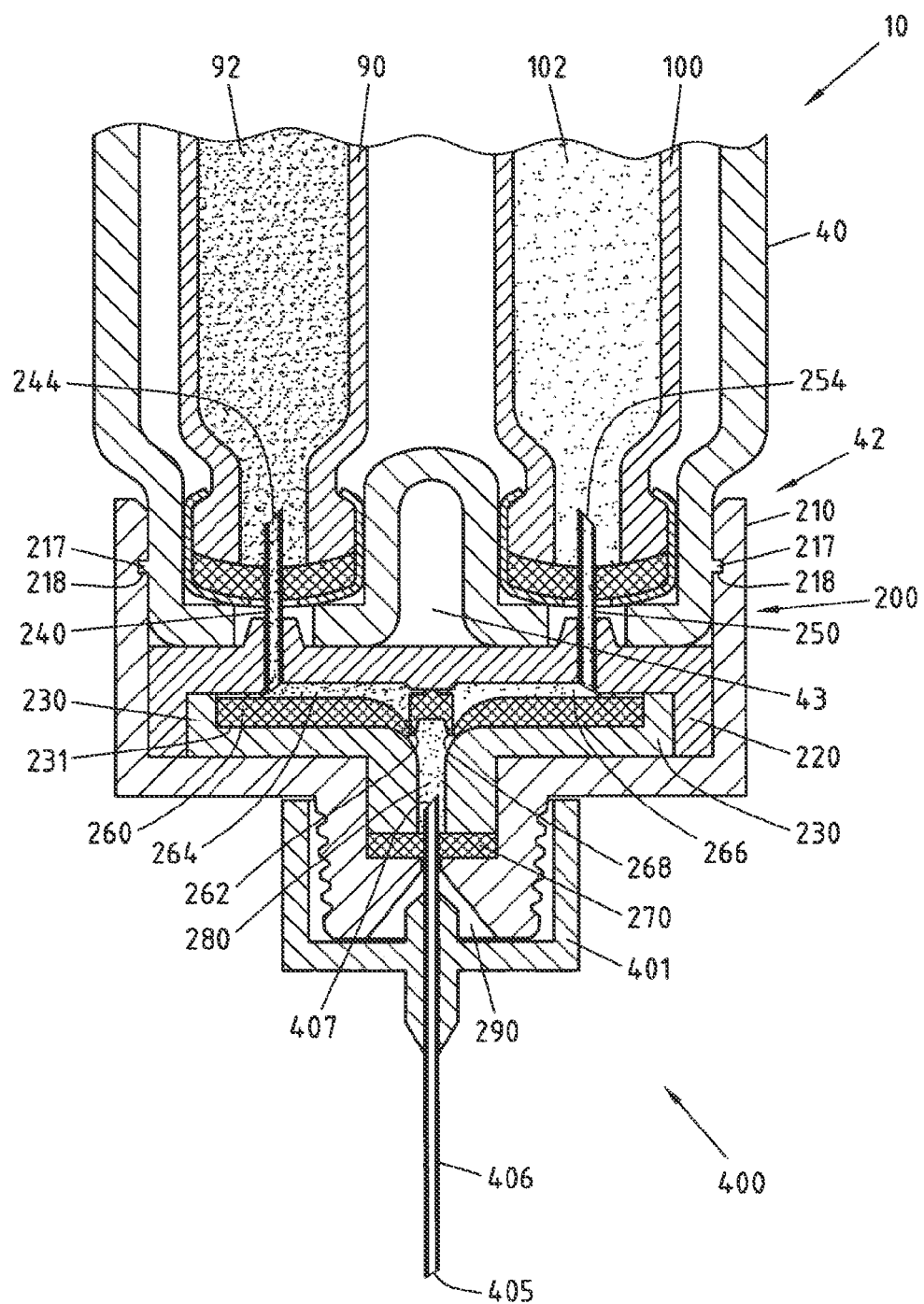
FIG. 4 illustrates a cross-sectional view of the dispense interface and dose dispenser mounted onto a drug delivery device, such as the device illustrated in FIG. 2.

A dose dispenser or needle assembly that may be used with the interface 200 is also illustrated and is provided in a protective outer cap (not shown). The dispense interface 200 illustrated in FIG. 4 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

FIG. 4 also shows a needle assembly 400. This has a double ended needle 406 and a hub 401. The double ended needle or cannula 406 is fixedly mounted in a needle hub 401. This needle hub 401 comprises a threaded (not shown) inner wall to allow the needle hub 401 to be screwed onto the dispense interface 200 which, in one preferred arrangement, is provided with a corresponding outer thread along a distal hub. Alternative releasable connectors may also be provided such as a snap lock, a snap lock released through threads, a bayonet lock, a form fit, or other similar connection arrangements. The double ended needle 406 is mounted centrally through the needle hub 401 such that a first or distal piercing end 405 forms an injecting part for piercing an injection site (e.g., the skin of a user). Similarly, a second or proximal piercing end 407 protrudes from an opposite side of the assembly 400. This second end 407 pierces a septum 270 of the dispense interface 200.

The dispense interface 200 is shown in cross-section in FIG. 4. In this one preferred arrangement, this interface 200 comprises: a) a main outer body 210; b) a first inner body 220; c) a second inner body 230; d) a first piercing needle 240; e) a second piercing needle 250; f) a valve seal 260; and g) the septum 270.

The dispense interface 200 is configured to be removably connected to the cartridge holder 40 by way protrusions 217 provided on the cartridge holder 40 and corresponding recesses 218 provided on the dispense interface. These co-operate to form an interference fit, form fit, or snap lock between the dispense interface 200 and the cartridge holder 40. Alternatively, and as those of skill in the art will recognize, any other similar connection train that allows for the dispense interface and the cartridge housing 40 to be axially coupled could be used as well.

The dispense interface 200 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

In addition, as can be seen in FIG. 4, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 4 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with the pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle 406), the output fluid path allows both medicaments to be in fluid communication with the attached needle assembly.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively. FIG. 4 illustrates the dispense interface 200 mounted onto the distal end 42 of the cartridge holder 40. The cartridge holder 40 is illustrated as having a first cartridge 90 containing a first medicament 92 and a second cartridge 100 containing a second medicament 102.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

It will be apparent that when the medical device 10 is brought into use for the first time there will be air in the first and second fluid conduits 264, 266 and the holding chamber 280 of the dispense interface 200 as well as the cannula 406 of the needle hub 400. Consequently, it is desirable to prime the device 10 by ejecting medicament through the conduits until medicament appears at the distal end of the needle hub 400; thereby ensuring that air has been expelled from the fluid communication channels between the cartridges 90, 100 and the end of the cannula 406 to be inserted into a patient. Furthermore, in the event of replacement of one or both of the cartridges 90, 100, it may be a functional requirement programmed into the device that the dispense interface 400 be removed before either one of the retainers 50, 52 can be unlocked. In this case, the device 10 will require priming after replacement of the cartridge and replacement of the dispense interface 200 or a new dispense interface 200. The volume of the conduits within the dispense interface 200 to be filled during priming may be in the order of 1 μl.

Figure 5:
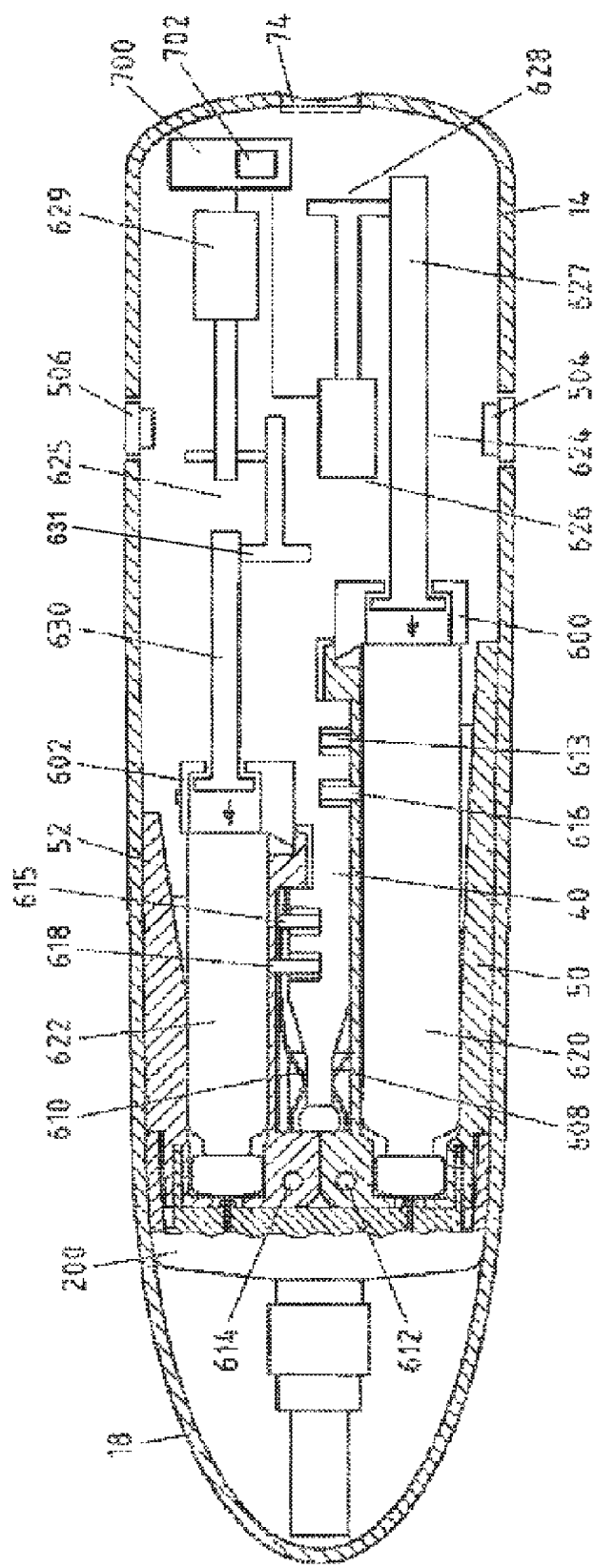
FIG. 5 is a cross-sectional view of the medical device showing medicament cartridges and a drive train.

FIG. 5 illustrates the medical device 10 in cross-sectional view. The two cartridge retainers 50 and 52 are illustrated in the closed position. Retainer 50 is configured so as to contain medicament reservoir 620, whereas retainer 52 is configured so as to contain medicament reservoir 622. The reservoirs 620, 622 may be glass, metal or plastic cartridges. Reservoir 622 may have a smaller diameter and a shorter length than reservoir 620. The cartridge holder 40 may further comprise two locking devices 600 and 602. The locking devices 600 and 602 may be designed as latches, which may lock the cartridge retainers 50, 52 in a form-fitting manner in their closed position. The locking devices 600 and 602 may be released or unlocked by operation of retainer door or cartridge release buttons 504 and 506. The retainer door or cartridge release buttons 504 and 506 may work mechanically or electromechanically.

The cartridge holder 40 further contains two cartridge retainer springs 608 and 610, which in the closed position of the cartridge retainers 50 and 52 exert an elastic spring force on the cartridge retainers. By releasing the locking devices 600 and 602 the spring force causes the cartridge retainers 50 and 52 to move in the open position. Cartridge retainer 50 is hinged to the cartridge retainer housing at pivot bearing 612, whereas cartridge retainer 52 is hinged to the cartridge retainer housing at pivot bearing 614. The cartridge retainers 50, 52 are thereby pivotable about the pivot bearings 612, 614 between their closed and their open position.

Retainer sensors for each of the retainers 50 and 52 may be provided and configured to detect the insertion condition of the respective medicament cartridges 620, 622 and/or the closing condition of the cartridge retainers 50 and 52. In the embodiment of FIG. 5, the retainer sensors which are provided in the cartridge holder 40 are shown to comprise position sensors 613 and 615 for sensing whether the retainers 50 and 52 respectively are in a closed or open position. Separate cartridge sensors or detect switches 616 and 618 are provided for sensing the presence or absence of a cartridge in the retainers 50 and 52 respectively. The position sensors 613, 615 are located in the device in a location that is separate from the retainer door latches 600, 602.

The device 10 further comprises a controller 700, which may be a micro-processor control unit. The controller 700 receives signals from the position sensors 613, 615 and cartridge sensors 616, 618.

An output from the cartridge sensor 616 for the cartridge 620 may indicate that the cartridge is correctly located within the device. This condition is most likely to occur when the cartridge retainer 50 of the device is closed with the cartridge 620 inserted. When either the cartridge retainer 50 is closed and the cartridge 620 is absent or the cartridge retainer 50 is open the controller 700 should detect that the cartridge is absent. The position switch 613 indicates that the cartridge retainer 50 is either open or closed, regardless of the presence or absence of a cartridge.

The conditions indicated in table 1 below can be achieved with a combination of the respective cartridge sensors 616, 618 and the respective position sensors 613, 615. For the purposes of describing the intended behaviour of the system, a '1' in the cartridge sensor column indicates that a cartridge has been detected and a '1' in the position sensor indicates that the door is closed. A '0' in either of these columns has the opposite sense to a '1'.

The table 1 below shows possible combinations of cartridge and retainer sensors.

TABLE 1

Cartridge and Cartridge retainer sensor states

| Condition | Cartridge Sensor | Retainer Sensor | Typical condition when the sensor combination occurs |
|---|---|---|---|
| A | 0 | 0 | The retainer is open with the cartridge either inserted in the retainer or removed from the retainer. These are conditions expected during a cartridge change event. |
| B | 0 | 1 | The retainer is closed but there is either an incorrect cartridge or no cartridge located in the door. This is the condition expected when the doors have been shut without a cartridge loaded, during storage for example. |
| C | 1 | 0 | The retainer is open and the device has detected the presence of a cartridge. This is an ERROR condition and will be reported on the user interface. |
| D | 1 | 1 | The retainer is closed and a cartridge has been detected. This is the condition expected for dose delivery. |

The outputs from these sensors may be subject to transitional states, for example, if the cartridge retainer 50 is closed with a cartridge in place, either the position sensor 613 or the cartridge sensor 615 may trigger first. The transitional states may be due to, for example, tolerances. So, depending on which sensor switch triggers first, the controller 700 may determine states: "cartridge retainer closed—no cartridge"; or the "cartridge retainer open—cartridge present", the latter being an illogical state.

The configuration and behaviour of the sensors for cartridge 622 is essentially the same as for cartridge 620 described above.

The device 10 further comprises a memory unit, for example a read-only memory unit being connected to controller 700, which may have programmed therein software to be executed by the controller 700 for performing the functions of the device, as will be described in more detail with reference to FIGS. 7 and 8 below. The controller 700 may comprise an evaluation unit 702, which may be configured to receive signals from the position sensors 613 and 615 as well as from the cartridge detect switches 616 and 618. The evaluation unit 702 may also be configured to receive signals from sensors that are configured to determine the filling level of the cartridges 620, 622.

The controller 700 is further connected to a user interface, for example the control panel region 60. Preferably, the control panel region 60 comprises output means such as the digital display 80 and input means such as dose setting buttons 62 and 64 or the button 66 designated with the symbol "OK" (shown in a different position in the embodiment of FIGS. 1-3 from the embodiment of FIG. 7). At the proximal end of the main body 14, an injection button 74 is provided.

FIG. 5 also shows a pair of drive trains 624 and 625. The first drive train 624 of the pair includes a motor 626 that drives a piston rod 627 via a gear 628. The drive train 624 is operative to drive the piston rod 627 under the control of the controller 700 to dispense medicament from the cartridge 620. A second drive train 625 includes a motor 629 for driving a piston rod 630 via a second gear mechanism 631, to dispense medicament from the cartridge 622 also under the control of the controller 700.

Figure 6C:
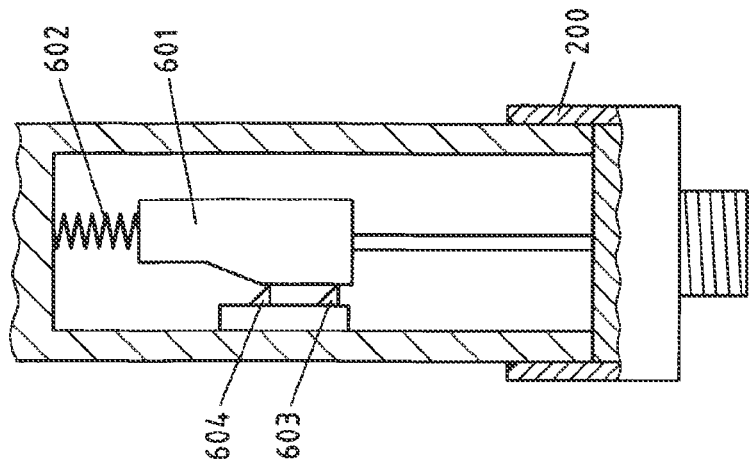
FIGS. 6a to 6c are cross-sectional views for illustrating attaching of the dispense interface to the device.
Figure 6B:
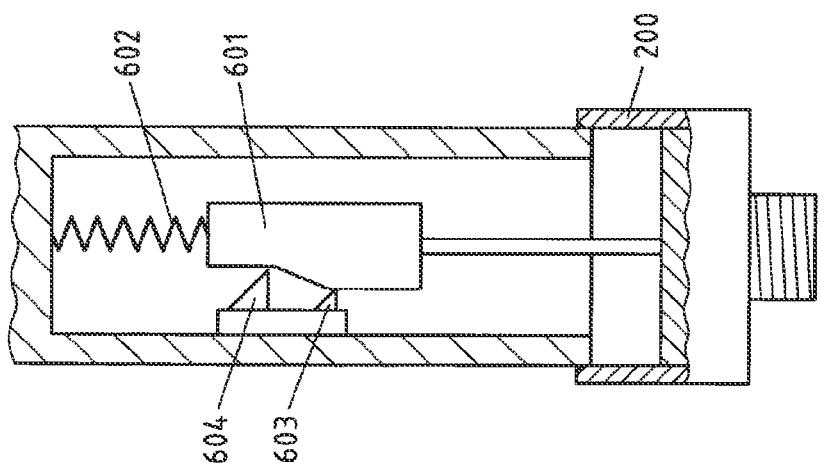
Figure 6A:
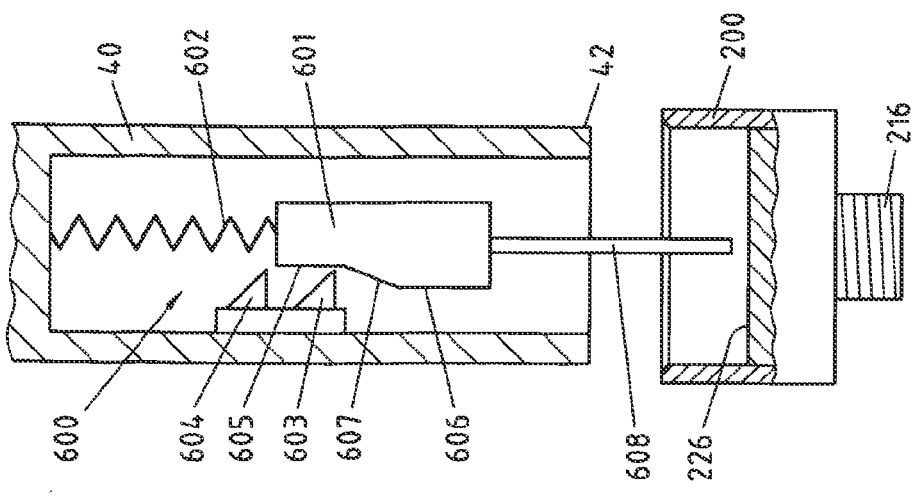

FIGS. 6a to 6c are schematic cross-sectional views of the dispense interface 200 showing an interface sensor 600. This may comprise a push rod 601. For instance, the interface sensor 600 is at least partially arranged in a cavity formed by the cartridge holder 40 such as cavity 43 in FIG. 4.

At the proximal end of the push rod 601, a spring 602 is arranged which is connected to the cartridge holder 40 such that the push rod 601 is resiliently hold in the drug delivery device 10 and is at least longitudinally movable in the drug delivery device.

The detecting arrangement 600 may further comprise a first switch 603 and a second switch 604 which are longitudinally arranged at a side-wall of the cavity 43. Therein, the first switch 603 is arranged closer to the distal end 42 of the cartridge holder 40 than the second switch. In other words, the first switch 603 is distally positioned and the second switch 604 is proximally positioned in the drug delivery device 10. The first switch 603 and the second switch 604 are pressure activated switches forming a first and a second detecting unit. In particular, the first switch 603 and the second switch 604 are only activated, when pressure is applied on the respective switch, and otherwise deactivated. The switches may be connected to a micro-processor control unit of the drug delivery device 10, for instance (logically signalling activation and deactivation to the micro-processor control unit).

A lateral surface of the push rod 601 oriented towards the first switch 603 and the second switch 604 is formed from three portions, two parallel surface portions 605, 606 and an inclined surface portion 607. The inclined surface portion 607 is arranged between the parallel surface portions 605, 606 such that the parallel surface portion 605 at the proximal end of the push rod is set back. A rod 608 is arranged at the distal end of the push rod 601.

In FIG. 6a the dispense interface 200 is not attached to the drug delivery device 10. In particular, there is no contact between the rod 608 and the surface 226 of the dispense interface 200. Accordingly, the spring 602 is relaxed and the push rod 601 is hold in a first position in the drug delivery device 10. In this first position of the push rod 601 in the drug delivery device 10, the first switch 603 and the second switch 604 face the set back parallel surface portion 605 and the spring 602, respectively. In particular, there is no contact between the lateral surface of the push rod 601 and the first switch 603 and the second switch 604. Both switches are deactivated.

In FIG. 6b, attachment of the dispense interface 200 to the drug delivery device 10 is initiated, the dispense interface 200 is aligned to the distal end 42 of the cartridge holder 40 and pushed towards the drug delivery device 10 to axially slide over the distal end 42 of the cartridge housing 40 of the drug delivery device 10. Thereby, the distal end of the rod 608 resides on the surface 226 of the dispense interface 200 and is also pushed towards the drug delivery device 10 such that, during attaching the dispense interface 200 to the drug delivery device 10, the movement of the dispense interface 200 towards the drug delivery device facilitates a corresponding movement of the push rod 601 and a compression of the spring 602.

When the push rod 601 is correspondingly moved, the first switch 603 and the second switch 604 slide along the inclined surface portion 607 of the lateral surface of the push rod 601 towards the parallel surface portion 606 and, thereby, increasing pressure is applied on the switches. When a pressure threshold is overcome, the first switch 603 and the second switch 604 are activated, for instance, the switches are activated, when residing on the parallel surface portion 606 (i.e. an activating portion of the push rod). Due to its distal position, the first switch 603 resides on the parallel surface portion 606 before the second switch 604 resides thereon and is, thus, earlier activated. When the attaching is initiated as illustrated in FIG. 6b, the first switch 603 resides on the parallel surface portion 606 and is activated.

In FIG. 6c, attaching of the dispense interface 200 to the drug delivery device 10 is completed such that the septae of the first cartridge 90 and the second cartridge 100 are pierced and the dispense interface resides in fluid communication with the primary medicament 92 of the first cartridge 90 and the secondary medicament 102 of the second cartridge 100 as described above.

When the attaching of the dispense interface 200 to the drug delivery device 10 is completed as illustrated in FIG. 6c, the second switch 604 also resides on the parallel surface portion 606 and is activated. The spring 602 is compressed and the push rod is in a second position.

When the dispense interface 200 is released from the drug delivery device 10, the compressed spring 602 relaxes and moves the push rod 601 back to the first position and optionally the dispense interface 200 to a detent position (i.e. the position illustrated in FIG. 6b). Thereby, firstly the second switch 604 and then the first switch 603 slide along the inclined surface portion 607 towards the set back parallel surface 605 and are subsequently deactivated. This enables the controller 700 to sense detachment of the dispense interface 200.

Although FIGS. 6a to 6c show two switches 603, 604, embodiments may employ a single switch for the interface sensor 600.

The operation of devices embodying the present invention will be described with reference to FIGS. 7 and 8.

Figure 7:
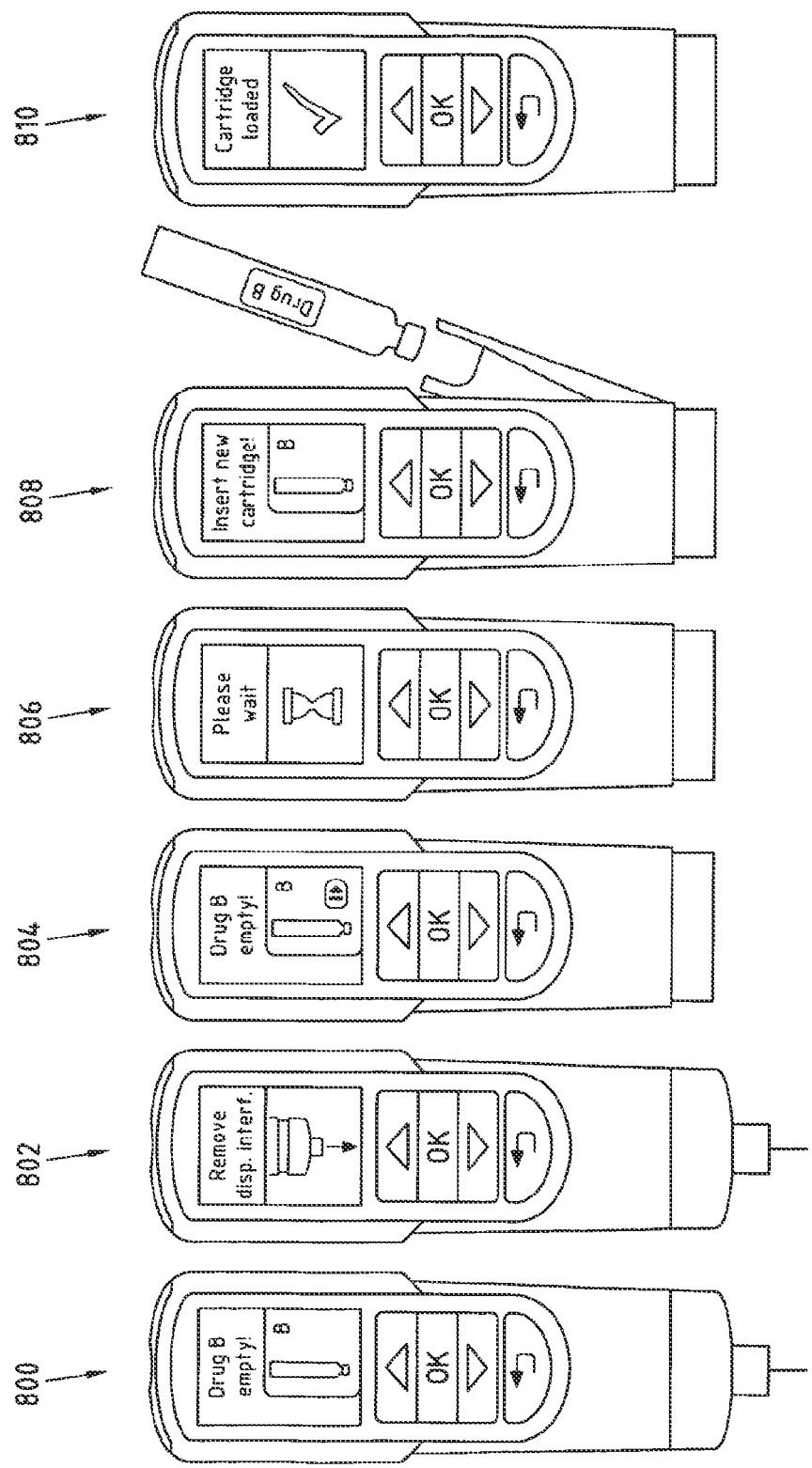
FIG. 7 is a cross-sectional view of the attaching or detaching of a dispense interface from the medical device.

FIG. 7 illustrates the process of exchanging a cartridge in a medical delivery device 10. In step 800 the controller 700 of the medical device 10 determines that the cartridge in retainer 50 is empty, or the user chooses to replace the cartridge, and so the controller 700 goes into a 'cartridge exchange or replacement mode'. For example, the device may inhibit the setting of a dose that is greater than the medicament remaining in the cartridge. Accordingly, the digital display 80 indicates that drug B (medicament cartridge 620) is empty. Likewise in step 800 the digital display 80 illustrates the cartridge 620 which has a big diameter and a great length as being the one that needs exchanging.

Before the user is allowed access to the cartridge holder 50, the device instructs the user to remove the dispense interface at step 802. This corresponds to step 900 of FIG. 8 and is indicated on the digital display 80. The indications on the digital display 80 shown in steps 800 and 802 may alternate during a certain period. Subsequently, the dispense interface 200 is removed from the cartridge holder 40 in step 802 by the user.

Figure 8:
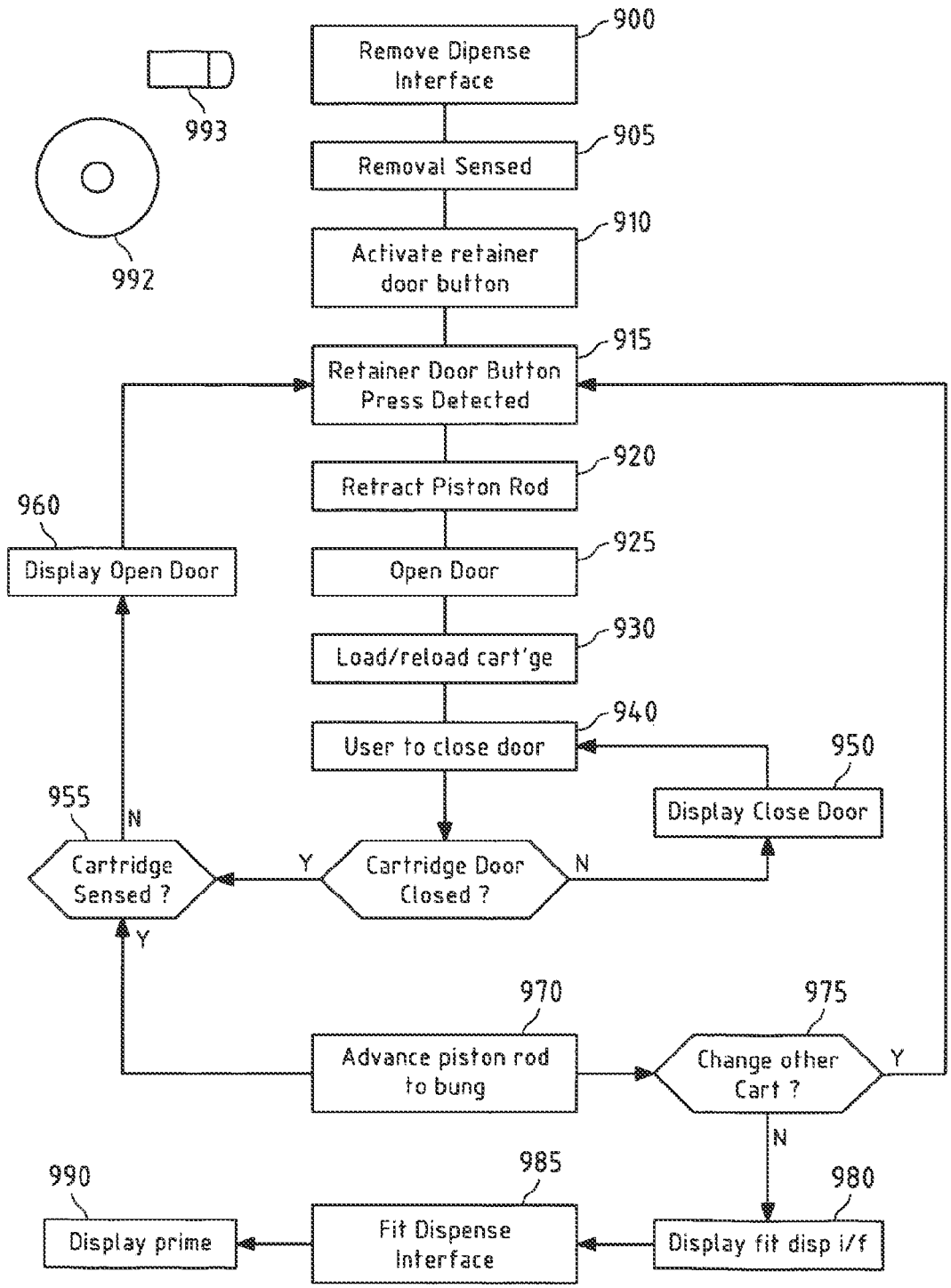
FIG. 8 is a flow chart illustrating operation of a device embodying the present invention.

In step 804 the controller 700 determines the dispense interface 200 being removed from the cartridge holder 40 by sensing signals from the switch or switches 603 and 604, as indicated by step 905 in FIG. 8. Further in step 804 the controller 700 may operate the locking devices 600 and 602 into an unlockable condition, in case they have been in a not-unlockable condition while the dispense interface 200 has been attached to the cartridge holder 40. At the same time the controller 700 activates the retainer door or cartridge release button 504 (step 910) corresponding to the cartridge to be exchanged, that is, cartridge 620. The controller 700 displays a prompt on the digital display 80 for the user to operate the cartridge release button 504. When the user presses the cartridge release button 604, this is sensed at step 915 whereupon the controller 700 causes the drive train 624 to retract the piston rod 627 (step 920) from the cartridge 620, displaying a "Please wait" instruction (shown as a rotating hour glass in 806 of FIG. 7) on the display as the piston rod 627 is retracted from the cartridge 620. When the piston rod 627 is fully retracted, the motor 626 stalls and a signal is sent to the controller 700 to trigger the locking device 600 into an unlocked or released condition thus allowing the opening of the cartridge retainer 50 (step 925 "Open Door). In the event that there is no cartridge in the retainer, the drive train may rewind by a small distance sufficient to release the latch. At the time of the motor stall, an encoder (not shown) for monitoring the drive train is put into a "datum reset" condition by the controller 700. Also, at this time, the locking device 602 is operated into a non-unlockable condition, in case this has not been conducted before so that only one cartridge retainer 50, 52 can be opened at a time.

In step 808 the cartridge retainer 50 is pushed out of the closed position into the open position by the cartridge retainer spring 608. It is also possible that cartridge retainer 50 is pulled out into the open position by the user, without the aid of elastic spring forces. As soon as the cartridge retainer 50 has been opened, the detection switch 616 sends an according signal to the controller 700. The digital display 80 subsequently indicates to insert a new cartridge 622, filled with drug B, and illustrates a cartridge which has a big diameter and a great length (step 930). At step 930, the user may load a new cartridge, close the retainer door leaving the retainer empty or even reinsert the existing cartridge.

Opening of the cartridge retainer 50 is sensed by the controller 700 whereupon the motor 626 is run for sufficient time to advance the piston rod 627 by a distance that will permit resetting of the locking device 600 when it is closed by the user after cartridge replacement. The detection switch 616 associated with the retainer 50 is provided to detect the presence of the cartridge 620 in the retainer 50 when closed. In the subsequent step 810 the cartridge retainer 50 is manually moved into the closed position (step 940), where it is locked by the locking device 600. When the retainer 50 is closed, the controller 700 senses a signal from the position sensor 613 provided to detect closure of the retainer 50. If the retainer 50 is not fully closed, no signal from the position sensor 613 will be sensed by the controller (step 945) and so the controller will provide an indication on the display 80 to close the retainer door (step 950). When in the closed position, this is sensed by the controller 700 (step 945). The controller 700 requires sensing of an output from the detection switch 616 to confirm the presence of a cartridge in the retainer 50 at step 955. If a replacement cartridge is detected by the detection switch 616, a corresponding signal is sensed by the controller 700 at step 955. If a cartridge is not sensed at step 955, a prompt is displayed at step 960 for the user to press the retainer door button, which in turn is detected at step 915. The prompt may additionally or instead correspond to the prompt illustrated at 804 of FIG. 7.

After successful placement of a new cartridge 620 in the retainer 50 and successful closure of the retainer 50, the detection switch 616 signals to the controller 700 that a cartridge is present and the position sensor 613 sends a signal to the controller that the door is closed. The successful insertion condition of the inserted cartridge may furthermore be indicated on the digital display 80 (see step 810 of FIG. 7), whereupon the controller advances the piston rod to the bung of the replacement cartridge at step 970. The cartridge exchange process described above may be applicable to the other cartridge 622 and its replacement into cartridge retainer 52 according to a routine of steps that corresponds to steps 800 to 810 (and steps 900 to 990 of FIG. 8) described above. If the device is operative to detect that the other cartridge is also empty or requires changing, then at step 975 this will be indicated on the display 80 as in step 800, but indicating Drug A instead of Drug B. The controller will activate the retainer door button 506 corresponding to this cartridge whereupon pressing of this button may be detected at step 915. If the device does not indicate change of the other cartridge, the user may still access it by pressing the retainer door button 506. If the other cartridge is not to be replaced, the controller 700 causes display of a prompt for the display interface to be fitted at step 980. Fitting of the dispense interface is detected whereupon the controller may display at step 990 a prompt for the user to implement a priming operation.

The steps 800 to 810 (and steps 900 to 990) described with reference to FIGS. 7 and 8 are applicable to the device of FIG. 1 having a single cartridge retainer.

The operational sequences of FIG. 7 or 8 may be performed by a computer program that may be stored on a computer-readable medium such as a CD-ROM 992 or a memory stick 993.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬ decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative; or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, θ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A medicament delivery device for the administration of one or more drug agents, wherein the device comprises:
    a retainer for holding a medicament cartridge, the retainer being moveable between an open and closed position;
    a position sensor for generating a position output indicative of whether the retainer is in an open or closed position;
    a cartridge sensor for generating a cartridge output indicative of whether the retainer is holding a medicament cartridge;
    a piston rod and drive train;
    a controller for controlling a predetermined operation of the device in dependence on an output of the position sensor and on an output of the cartridge sensor;
    a dispense interface for providing fluidic communication between an outlet and a medicament cartridge retainer;
    an interface sensor for generating an output indicative of whether the dispense interface is attached to or detached from the device;
    a latch movable under control of the controller between a latched position, for holding the retainer in said closed position, and an unlatched position, for allowing opening of the retainer to the open position; and
    a cartridge door button;
    the controller being operative for controlling a predetermined operation of the device in dependence on an output of the interface sensor, wherein the predetermined operation relates to a cartridge change cycle of the device upon detachment of the dispense interface,
    wherein, in response to receiving an output from the interface sensor indicating that the dispense interface is detached from the device, the controller is configured to initiate the cartridge change cycle,
    wherein initiating the cartridge change cycle comprises:
        activating said cartridge door button; and
        in response to detecting that the activated cartridge door button has been actuated by a user, retracting the piston rod from the medicament cartridge and moving the latch from the latched position to the unlatched position.

2. A medicament delivery device according to claim 1, wherein the controller facilitates control of different predetermined operational sequences depending on the outputs from the cartridge and position sensors.

3. A medicament delivery device according to claim 2, wherein a first predetermined operational sequence is implemented by the controller when the cartridge sensor indicates that the retainer is holding a medicament cartridge and the position sensor indicates that the retainer is in a closed position, and the first one of said predetermined operational sequences includes advancing the piston rod to the medicament cartridge.

4. A medicament delivery device according to claims 2, wherein a second predetermined operational sequence is implemented by the controller when the cartridge sensor indicates that the retainer is not holding a medicament cartridge and the position sensor indicates that the retainer is in a closed position, and wherein the second predetermined operational sequence includes displaying a prompt to insert a cartridge in the device.

5. A medicament delivery device according to claim 1, wherein the device is hand-held.

6. A medicament delivery device according to claim 5, wherein the device is a pen-type injection device.

7. A medicament delivery device according to claim 1 comprising first and second retainers each for holding a medicament cartridge.

8. A method of controlling a medicament delivery device having a dispense interface, comprising: sensing detachment of the dispense interface from the device; activating a cartridge door button in response to sensing detachment of the dispense interface from the device; sensing actuation of the activated cartridge door button in response to the sensed detachment of the dispense interface and retracting a piston rod from a medicament cartridge retainer of the device in response thereto; opening the medicament cartridge retainer following retraction of the piston rod; sensing outputs of a cartridge sensor and a medicament cartridge retainer position sensor; and either advancing the piston rod towards the medicament cartridge when the output of the cartridge sensor indicates the presence of a cartridge and the output of the medicament cartridge retainer position sensor indicates the retainer is in a closed position, or prompting insertion of a medicament cartridge when the output of the cartridge sensor does not indicate the presence of a cartridge when the position sensor indicates that the retainer is in the closed position.

* * * * *